(12) United States Patent
Petrich et al.

(10) Patent No.: US 7,369,952 B2
(45) Date of Patent: May 6, 2008

(54) QUANTIFICATION OF DISEASE PROGRESSION BY MEANS OF INTERPOLATION BETWEEN PARAMETERS BASED ON ELECTROMAGNETIC SPECTRA

(75) Inventors: Wolfgang Petrich, Bad Schoenborn (DE); Gerhard Werner, Weinheim (DE); Heinz-Michael Hein, Darmstadt (DE); Hans-Juergen Kuhr, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 273 days.

(21) Appl. No.: 10/552,248

(22) PCT Filed: Apr. 6, 2004

(86) PCT No.: PCT/EP2004/003613

§ 371 (c)(1),
(2), (4) Date: Oct. 6, 2005

(87) PCT Pub. No.: WO2004/090779

PCT Pub. Date: Oct. 21, 2004

(65) Prior Publication Data

US 2006/0195296 A1 Aug. 31, 2006

(30) Foreign Application Priority Data

Apr. 8, 2003 (DE) .............................. 103 15 877

(51) Int. Cl.
*G01R 23/16* (2006.01)
*G06F 19/00* (2006.01)

(52) U.S. Cl. ...................................... 702/76
(58) Field of Classification Search .................. 702/76
See application file for complete search history.

(56) References Cited

U.S. PATENT DOCUMENTS 5,290,705 A    3/1994  Davis ........................ 436/164
5,435,309 A *  7/1995  Thomas et al. ............. 600/310
5,734,587 A *  3/1998  Backhaus et al. ............. 702/25

(Continued)

FOREIGN PATENT DOCUMENTS

DE          4331596 A1        3/1995

(Continued)

OTHER PUBLICATIONS

Lisboa et al. "Pattern Recognition Methods for MRS Analysis and Classification", Jun. 24, 1997, IEEE, pp. 3/1-3/9.*

(Continued)

*Primary Examiner*—John Barlow
*Assistant Examiner*—Cindy D. Khuu
(74) *Attorney, Agent, or Firm*—McDonnell Boehnen Hulbert & Berghoff LLP (57) ABSTRACT

The invention relates to analysis methods for diagnosing diseases on human and animal samples. Said invention also relates to an evaluation method for diagnosing the individual stages of a disease in such a way that it is possible to display the progression thereof. Said invention also makes it possible to identify diseases in an early manner and to carry out therapeutic controls. The inventive method consists in carrying out actually known multivariable evaluation methods for classifying samples. Nevertheless, the invention is characterised in that no sample is allocated to a certain class, but it is classified in a data record based on the interpolation between different classes.

19 Claims, 4 Drawing Sheets

U.S. PATENT DOCUMENTS

| | | |
|---|---|---|
| 5,869,001 A | 2/1999 | Backhaus et al. |
| 6,518,069 B1 | 2/2003 | Otvos et al. |
| 2003/0162301 A1* | 8/2003 | Noergaard et al. .......... 436/172 |

FOREIGN PATENT DOCUMENTS

| | | |
|---|---|---|
| EP | 0 644 412 A | 3/1995 |
| WO | WO 97/18566 A1 | 5/1997 |
| WO | WO 99/00660 A1 | 1/1999 |
| WO | WO 00/65366 A | 11/2000 |
| WO | WO 01/92859 A | 12/2001 |
| WO | WO 02/23971 A | 3/2002 |
| WO | WO 02/41234 A | 5/2002 |
| WO | WO 02/057753 A2 | 7/2002 |
| WO | WO 02/066963 A2 | 8/2002 |
| WO | WO 02/086478 A | 10/2002 |
| WO | WO 03/060515 A1 | 7/2003 |

OTHER PUBLICATIONS

Nikulin, et al., "Near-optimal region selection for feature space reduction: novel preprocessing methods for classifying MR spectra," *NMR in Biomedicine*, 11:209-216, 1998.

Petrich, "Mid-Infrared and Raman Spectroscopy for Medical Diagnostics," *Applied Spectroscopy Reviews*, 36 (2 and 3):181-237, 2001.

* cited by examiner

QUANTIFICATION OF DISEASE PROGRESSION BY MEANS OF INTERPOLATION BETWEEN PARAMETERS BASED ON ELECTROMAGNETIC SPECTRA

BACKGROUND

1. Field

The invention relates to the field of analytical methods suitable for diagnosing diseases with human or animal samples. To analyze the samples, electromagnetic spectra are recorded, stored and analyzed by multivariate analytical methods. The diagnosis of diseases using multivariate analytical methods is already known in the prior art and is explained in greater detail below. However, with the help of the inventive method, it is also possible for the first time to reliably detect individual manifestations of a disease syndrome in addition to detecting a specific disease. The inventive method thus makes it possible for the first time to diagnose individual stages of progression of a disease; this could provide information regarding the development of a disease, for example, or might reflect the effects of therapeutic methods on a patient's health status.

2. Description of the Related Art

In the prior art, most diagnostic methods are currently based on detection of individual characteristic substances in a sample to be analyzed to obtain information regarding a disease. These substances are detected in blood, urine or other body fluids, for example. Substances characteristic of a disease include, for example, disease-induced metabolites which accumulate in the body and can be detected in the blood. Samples taken from patients are analyzed by clinical analytical methods or by spectroscopic methods and are correlated with the patient's disease symptoms. On the basis of these findings, a medical diagnosis is made, taking into account the analytical results obtained on the sample as well as the patient's disease symptoms.

Frequently, however, it is found that diagnosing individual diseases is particularly difficult because the substances to be analyzed for the disease cannot be determined unambiguously or are even unknown. A diagnosis of such diseases can often be ensured only through complex analyses of varied parameters which provide an indication of the disease. For example, the so-called metabolic syndrome is an example of a disease that is difficult to diagnose; it is assumed that at least one of ten adults in the United States suffers from this syndrome. This disease is thus one of the most common health anomalies in western civilization. Metabolic syndrome involves an accumulation of five different risk factors for having a high cardiovascular mortality. Metabolic syndrome is diagnosed when a patient has at least three of five risk factors. The risk factors, i.e., parameters for detection of this disease, include obesity, hypertension, elevated cholesterol levels, elevated blood sugar and blood lipid levels. The example given here shows that five different tests are necessary to allow this disease to be diagnosed.

To simplify such complex test methods and gain a greater diagnostic certainty, methods of disease analysis have been developed that allow a reliable diagnosis to be made with just one measurement method even without a knowledge of a definite substance characteristic of a disease. These methods are performed by IR spectroscopy, for example, and utilize multivariate analytical methods, among others. With the help of multivariate analytical algorithms, it is possible thereby to perform a pattern recognition on spectra without having to perform a characterization of individual substances. Multivariate analytical methods make it possible to analyze an unknown sample with a high reliability and correlate it with various diseases as a function of a previously trained database. To compile the database, samples are first taken from patients having a specific syndrome. The measured spectra are then allocated to a class characterizing the particular disease family. If infrared spectra are recorded on a plurality of samples or methods belonging to a known class according to identical or at least comparable measurement methods, then there may be training of the database. These spectra are supplied to the multivariate analytical method according to their classification so that the database includes characteristic spectra patterns, each belonging to a certain class and thus belonging to a disease family. The system is trained with the help of multivariate analytical algorithms until a distinction can be made between different classes. For example, in this way it is possible to categorize samples taken from healthy people or from people sick with an anomalous condition that is to be investigated. If an unknown sample is measured, the system is able to correlate the unknown sample with a class with sufficient reliability so that a diagnostic indication is given. This is preferably based on pattern recognition of the measured spectrum in a previously defined measured wavelength range, and an allocation of an unknown sample to a previously classified disease group (sick/healthy) is then made on this basis. The basic principles of such a method which permits classification of samples by IR spectroscopy and multivariate analytical methods are described in the document EP 0 644 412, for example.

In addition, use of such a method for analyzing metabolic syndrome is disclosed in the document WO 03060515 A1. To this end, spectra of healthy patients and spectra of patients suffering from metabolic syndrome are taken in a predetermined wavelength range, stored and classified in a database.

Depending on the analysis to be performed, a wavelength range in which characteristic spectra patterns permit a reliable allocation to one class is selected. For example, a determination of the particular wavelength range which has proven suitable for analyzing a certain disease syndrome can be done, e.g., by means of multivariate analyses or by algorithms such as those described in *NMA Biomedicine*, vol. 11, issue 4-5 (1998), pp. 209-216. Consequently, a correlation matrix is first set up in various analytical methods such as discriminance analysis and cluster analysis. The analytical method then determines which wavelengths are to be used with which influence for classification on the basis of the correlation matrix. The wavelengths used for analysis span a space that matches in dimension the number of wavelengths. A subspace in which the allocation of samples to classes can be performed unambiguously is then selected by the analytical method. This results in an allocation of samples to a class from their spatial proximity in said subspace. As soon as a scheme for classification according to a disease family has been developed, the data can be stored in the system, so that an analytical system can make suggested diagnoses for a plurality of diseases.

Multivariate analytical methods such as those known in the prior art are explained in greater detail below on the basis of the example of discriminance analysis.

Linear discriminance analysis permits a separation between two data records, which in the example cited here reflect, for example, patient data on a healthy patient and on a sick patient, with the goal of permitting a reliable differentiation between the data records. Practice has shown that there is often overlapping of data records, with a number of data possibly being allocated both to the "healthy" data record and also to the "sick" data record. There is thus no definite classification of this data, which may be referred to as the intersection of the "healthy" and "sick" data records in the example cited here. An allocation of unknown samples whose measured parameters are in this intersection range of the two data records is therefore impossible. Like other multivariate analytical methods, linear discriminance analysis draws a boundary between two data records to which an allocation is to be made. All data within this limit/these limit values belongs to the "healthy class," for example. The larger the data record of a class, the more sensitive is an allocation of an unknown sample in this class, so that almost all samples belonging to this class are also allocated to it. However, such a large data record also includes the allocation of samples that have been incorrectly allocated to this class so that a sensitive allocation will have a low specificity accordingly. Therefore, the object of such analytical methods is to achieve an optimized allocation, finding a balance between sensitivity and specificity. Training in the program is possible, increasing the sensitivity and specificity of the allocation by measurement and allocation of known samples. In practice, in the analysis the process parameters that characterize the sensitivity and specificity are cited according to the respective allocation. The values of unknown samples which are directly in an intersection of data records are evaluated as not analyzable in order to avoid an excessive error in the allocation. A diagnostic indication cannot be given for a sample whose parameters are within the intersection.

Consequently, one disadvantage of the prior art is that a disease can be diagnosed only with respect to different classes (e.g., "healthy" or "sick"), without being able to take into account data within the intersection, for example. Thus the course of a disease in a patient, which is continuous per se, is divided into two discrete steps which allow only a "healthy" or "diseased" condition as a diagnostic indication. It is thus impossible to take into account a real course of a disease having stages of the disease.

SUMMARY

The object of the inventive method is to prevent the disadvantages of the prior art as described here. In particular, the inventive method takes into account the continuous course of a disease and thus permits in particular an analysis of spectra within an intersection of data records. Consequently, the inventive method makes use of precisely the data that is not considered analyzable according to the prior art. For example, early detection of diseases and diagnosis of disease courses, etc. are made possible by the inventive method.

This invention includes a method for analyzing an electromagnetic spectrum, where the extend to which the electromagnetic spectrum belongs to a class is determined. This ensures that a real course of disease and/or health can be imaged, so that essential conclusions, e.g., regarding treatment can be made or measures can be taken to prevent disease.

The inventive method analyzes an electromagnetic spectrum generated by a measurement of an unknown sample. By means of a multivariate analytical method, a sample parameter that can be allocated to a data record is determined. The data record is calculated by interpolation between at least one portion of first data and at least one portion of second data, the first and second data each being allocated to a first class and second class, respectively. The first data includes a first parameter which has been generated by means of the multivariate analytical method on the basis of electromagnetic spectra of known samples belonging to the first class, thus permitting a reliable allocation of samples to the first class on the basis of the first parameter.

The second data similarly includes a second parameter which has also been generated by means of the multivariate analytical method on the basis of electromagnetic spectra of known samples belonging to the second class, so that a reliable allocation of samples to the second class is possible on the basis of the second parameter.

After allocation of the sample parameter to the data record, a proportion value for the sample parameter regarding at least a portion of the data record is determined. On the basis of this proportion value, a portion of the sample parameter is allocated to a class, so that the extent to which the unknown sample belongs to a class is determined.

The inventive method permits a continuous classification of a sample between different disease families. The course of a disease can be represented by a curve of the course of the interpolated data on the basis of the interpolation between data obtained in the late stage of a disease family, for example, and data that could be obtained from a healthy patient. Regarding the present invention, the interpolated data record is defined by a data range spanned by the interpolation between at least two values so that the data record includes at least one intermediate value defining the spanned data range between the known values. The known data between which an interpolation is performed belongs to the first and second classes according to this invention.

An allocation of measured data to a curve of the course of the interpolated data record makes it possible to image the disease stage of a sample accurately and thereby create a prognosis regarding the course of the disease, for example, or optionally to calculate a probability of a possible disease. Such a classification of a sample thus offers the possibility of reliably ensuring an early diagnosis, for example. This has proven essential to healing many diseases. The continuous differentiation of the disease syndrome here allows imaging of the prognosis of the course of diseases and monitoring of the particular acute manifestation without limiting the method to an exclusive allocation between two classes. An analysis of data within an intersection according to the prior art thus becomes possible.

The inventive method relates to the analysis of body fluids, cell suspensions and bacterial suspensions. Clinically relevant body fluids that can be analyzed with this method include, for example, blood, plasma, serum, hemolyzate, urine, cerebrospinal fluid, saliva, transpiration fluid, lacrimal fluid, cyst fluid, amniotic fluid, sputum, ascites and sperm. The terms "cell suspension" and "bacterial suspension" are understood to refer to samples obtained either directly (e.g., by biopsy, smear, etc.) or by culturing in a culture medium.

In particular, an inventive method is suitable for analyzing fluids containing a plurality of different ingredients. This is true in particular of blood, plasma, serum and hemolyzate.

Implementation of the inventive method begins with making available the sample fluid and/or suspension to be classified. This may be accomplished in a sufficiently known manner, e.g., by sampling a blood sample or urine sample. For some types of samples it is advantageous if they are conditioned before performing the method. Whole blood, for example, can be centrifuged to separate serum and blood cake.

The sample thus obtained may advantageously be applied to a carrier which makes it possible to record an infrared spectrum. Such a carrier may be, for example, a metallized microscope slide. Carriers having a reflective surface and a certain roughness to produce a diffuse scattering of infrared radiation are preferred. Carriers which are mirrorized on their surface to which the sample is applied may also be used. The carrier may be coated with metals, preferably noble metals such as gold, platinum, palladium, but also with base metals, preferably aluminum and chromium, for example. These coatings have the advantage that they are largely inert with respect to the sample and also with respect to ambient air. The carriers may have a planar surface to which the sample is applied. However, carriers having a well or other recess to accommodate the sample fluid are preferred according to this invention.

Suitable sample carriers are described, for example, in U.S. Pat. No. 5,734,587 for transmission measurements and for reflection measurements in U.S. Pat. No. 5,869,001.

Other preferred embodiments of sample carriers are described in the documents EP 0 644 412 and DE 4331596, for example.

In addition to carriers suitable for reflection measurement, carriers for transmission measurements that allow the incident light to pass through may also be used to advantage. These carriers may be made of plastics, for example, such as polycarbonate, polyethylene or polymethyl methacrylate, which are permeable for infrared radiation in a wide range of wavenumbers. These carriers for the transmission measurement may also have wells for the sample fluid like those for the reflection measurement. Measurements in diffuse reflection are advantageous in that inhomogeneities in the sample material, e.g., turbidities, that do not interfere with the analysis but actually support the diffuse reflection, are advantageous. To use the carriers described above, it has proven advantageous to dry the applied sample first before performing the measurement. Examples of drying the sample are disclosed for example in U.S. Pat. No. 5,869,001. However there is also the possibility of eliminating the drying step and performing the measurement directly on the liquid sample. Measurements on liquid samples are described for example in the document WO 02/057753 where the measurement is performed in transmitted light through a measurement cell with a thickness of a few µm.

In addition, measurements under attenuated total reflection (ATR) have proven suitable for the inventive method.

Arrangements for analysis of diffuse or direct reflection and for measurement of transmission are known in principle in the prior art and therefore will not be explained in greater detail here. An arrangement used for a analysis of diffusely-reflected radiation is described in detail in German Patent Application DE 4331596, for example.

In principle there are two different measurement techniques which are often used in spectroscopy for analyzing samples in the diagnostic field. Measurements for infrared spectroscopy are often performed here in the middle infrared range (2.5-25 µm). To record an infrared spectrum, the sample is illuminated with infrared radiation on the sample carrier. Infrared radiation in the wavenumber ranges already described can be generated with IR spectrometers available on the market, e.g., from Nicolet, Bruker and Perkin Elmer.

Depending on the sample to be analyzed, Raman spectroscopy is frequently used, but it has a much lower sensitivity for detection of an analyte in comparison with infrared spectroscopy. However, especially with biological samples, it is common to make use of the advantage here that, unlike infrared spectroscopy, water bands which cause only minor interference are superimposed on the analyte signal. Especially in the case of biological samples in which the water content is frequently very high, infrared measurements often lead to falsified analytical results because there is a strong absorption band of water in the middle infrared range. Despite the inferior sensitivity, Raman spectroscopy has thus proven to be a suitable method of spectroscopy under some circumstances. Detailed information regarding the aforementioned spectroscopy methods and possible applications is presented, for example, in the document by W. Petrich: "Mid-IR and Raman spectroscopy for medical diagnostics," *Appl. Spectros. Rev.* 36 (2001) pp. 181-237.

To largely minimize the absorption of water in infrared spectroscopy, it may prove advantageous to have the sample dried first on a sample carrier before performing the measurement, as already described. It has been found that drying usually does not cause any impairment of the sample which would make an analysis and classification impossible. Drying is, however, an important step to maintain the required high reproducibility of the recorded spectra.

Drying of the sample can be performed by simply evaporating the liquid at room temperature or under special conditions, e.g., by applying a vacuum, heating the sample or storing it in the presence of a desiccant. The term drying is understood here to refer essentially not to 100% drying of a sample so that the remaining moisture content of a dried sample amounts to only a few percent. The drying steps, as described, have the advantage that the sample develops a cohesive film without cracks or tears that could interfere with an analysis.

In drying a sample, a dry residue of varying form is obtained, depending on the drying conditions, the carrier and the type of sample. When drying serum samples on closed surfaces, a circular bulge usually is formed on the closed surface, its thickness decreasing in the direction of the center of the circle. In the case of self-supporting films, a bulge also develops in the boundary zones to the carrier material, developing into a relatively uniformly thick film toward the center of the opening.

IR light is directed at a sample in reflection and transmission preferably in such a way that the entire sample is included in the IR beam bundle. Because of this integral irradiation of the sample, the measurement is largely independent of the drying profile of the sample. This is another important factor that increases the reproducibility of the analysis of spectra.

If Raman spectroscopy is used as the analytical method, it is not necessary to have a drying step during sample preparation.

To record an infrared spectrum, the sample is illuminated with infrared radiation. The infrared light may be within the entire infrared range, i.e., approximately 400 $cm^{-1}$ to 15,000 $cm^{-1}$. In conjunction with the aforementioned drying method, IR spectroscopy in the range of 400 $cm^{-1}$ to 4,000 $cm^{-1}$ is especially advantageous because it has a high specificity in this range.

The radiation passing through the sample or reflected by the sample is picked up by a detector which should detect the largest possible amount of the radiation. Infrared-sensitive detectors such as bolometers, thermocouples, photovoltaic elements and semiconductor detectors are known in the prior art. Before the radiation reaches the detector, it may be passed through a system of lenses, apertures and mirrors.

The recording of infrared spectra is sufficiently well known in the prior art. With respect to recording IR spectra of dried samples, reference is made here to the German Patent Application DE 4331596.

With the usual methods of analyzing spectra, the transmitted or reflected radiation is recorded as a function of the incident wavelength. According to this invention, such a spectrum is analyzed by a multivariate analytical method for generating a sample parameter. Within the scope of the present invention, the term "spectrum" is understood to refer to any form of data structure generated by measurement of a sample as described here. It does not matter for the inventive analytical method whether the method is based on the data of an interferogram or the Fourier-transformed data resulting therefrom. For this analytical process, the spectrum must first be digitized unless it has already been recorded in digital form. This means that the spectrum is converted into a table of values containing the absorbance or transmittance for discrete wavenumbers. The number of value pairs depends essentially on the capacity of the available software and/or hardware. According to this invention it is not necessary to analyze individual bands from the spectrum and interpret them separately. However, it is proven advantageous for some analyses if the table of values used for the analysis is limited to certain ranges of wavenumbers. In principle, a variety of methods may be used for selection of wavelength ranges. Such methods are adequately well known in the prior art and are explained in EP 0 644 412 and WO 02/66963, for example. It is possible in this way to make a selection of relevant ranges of the spectra, and parts of the spectra that are of little informational value can be eliminated.

The digitized spectrum is provided for a multivariate analytical method available in the form of a computer program.

Multivariate analytical methods in the sense of the present invention include discriminance analyses, regularized discriminance analyses, neural networks, cluster analyses, etc. In principle, however, all conceivable multivariate analytical methods such as those adequate well known in the prior art may be used in performing the method according to this invention.

Said software packages can be obtained from the companies STSC, STAT SOFT, SAS and Galactic Industries, for example.

Before being used according to the present invention, the multivariate analytical methods must be trained for the area of use. This is usually done through a number of training runs in which infrared spectra of a plurality of samples of known classifications are input into the analytical method. Likewise, the analytical method is notified of the type of classification of the individual samples. In the aforementioned training run, the analytical algorithm automatically selects parameters that ensure a reliable allocation of samples to the specified classes. The parameters obtained in this way can be used in the remaining course to calculate the interpolated data record. It does not matter according to the present invention whether an interpolation is performed among the parameters directly or whether an interpolation is first performed between the spectral data before the parameters are generated. However, it is found that determining the parameters first and then performing the interpolation among the parameters greatly simplifies generation of the interpolated data record.

As a rule, the analytical system may include a plurality of different classes between which an interpolation can be performed according to this invention. The inventive method makes it possible to reflect the course of a disease by interpolation between data and thus also accurately image and track intermediate stages of a disease syndrome. With the help of the inventive method, the sample is classified in different curves for different disease courses which would have previously required a plurality of separate analytical processes using the methods available in the past. Classes that fall in the range of internal diseases are particularly important for the clinical analysis. For example it is possible with inventive methods to generate curves for disease courses that make it possible to predict whether or not a patient has a liver disease or a kidney disease. The classification of an unknown sample described here is not equivalent to an unambiguous diagnosis, however, because the same spectral changes in a sample may under some circumstances be caused by different diseases or dysfunctions. Instead, the said classification of the sample constitutes a screening method with which it is possible to decide which diseases the sample is to be tested for by using traditional methods. This eliminates the need for a plurality of analytical tests that would normally be necessary, e.g., for admission testing in a clinical laboratory.

In addition, the inventive method permits early detection of diseases that could not be performed under some circumstances by using traditional methods.

As will be shown in the following, by means of the inventive method it has become possible for the first time to image relationships between various diseases that were previously considered and treated independently of one another. It quickly becomes apparent that such newly obtained findings regarding the relationships among diseases previously considered to be independent will offer a variety of new options for treatment and care.

According to the present invention, the interpolation between two classes (e.g., healthy and sick) may be performed on the example of linear discriminance analysis, by calculating advantageously the distance between the discriminance function and the sample parameter of the sample to be analyzed in a multidimensional space. This space might be, for example, the space of the main components, and the distance could be defined by the Euclidean distance or the Mahalalobis distance. This measure of distance can be standardized over the entire training data record and be understood as a particular manifestation of an interpolation. As an alternative to this, the distance could be converted with the help of a probability function. Likewise it is conceivable to use the value of the discriminance function or a value of the discriminance function modified with the help of a probability function.

In the case of an analysis by neural networks, it is conceivable to standardize the weighting of the particular interconnection and/or neurons to the two starting neurons, e.g., to combine the sick and healthy classes, standardize them and then use a scaling of this standardized weighting between the two classes/starting neurons as an interpolation.

Here again, transformation with any function is conceivable, e.g., a probability function. In the case of a monitored classification as is the case with a neural network, it is also possible to implement one (or more) new classes in the training of the network—represented by one or more new starting neurons—and to use here such spectra which cannot be allocated adequately to either group A or group B (e.g., healthy or sick).

An interpolation between data on the basis of diabetes as a disease syndrome is illustrated below as an example. A interpolation is performed between first data belonging to a class referred to as "healthy," i.e., this data has been generated on the basis of known samples obtained from healthy patients or patients not suffering from diabetes, and second data generated on the basis of samples taken from patients with diabetes. Based on the particular data of each class, first, parameters are generated by means of a selected multivariate analytical method so that the parameters can each be allocated to the first and second classes, respectively. Then there is an interpolation between the parameters. It is advantageously found here that a course of a disease will correlate with the course of a curve of the interpolated data calculated in this way so that samples of patients taken in different stages of the disease can be allocated to the interpolated data record. If an analytical method is performed as described here, for example, then an unknown sample is analyzed first by means of the same multivariate analytical method to determine a sample parameter so that the sample parameter can be allocated to the data record obtained by interpolation between the first parameter and the second parameter. On the basis of this allocation, a portion value can then be determined for the sample parameter reflecting the extent to which the sample belongs to a class. For example, the proportion value of the sample parameter regarding to a class can be calculated as a percentage. This proportion value reflects the allocation of the sample parameter to a point in the curve of the interpolated data record. It is also conceivable for the proportion value to be depicted instead of a numerical value, e.g., graphically. An allocation of the sample parameter to the calculated curve according to the course of a disease thus illustrates graphically the patient's condition in terms of the disease. The physician is thereby given an indication of the disease state of the patient from whom the sample was taken with regard to this disease.

Tests have shown that in measurement of a sample from a patient suffering from metabolic syndrome, the parameters thereby generated can be allocated to the curve describing the course of diabetes. An allocation of the sample parameter of a patient having metabolic syndrome to the curve of a healthy person and a patient with diabetes thus permits the conclusion that metabolic syndrome is a precursor of diabetes. Thus there is a direct correlation between the disease "metabolic syndrome" and the disease "diabetes." This example illustrates clearly the new possibilities inherent in the method according to this invention. Prevention of the disease diabetes could thus be ensured at an early stage, e.g., by prescribing medication for hypertension, obesity or elevated cholesterol levels, etc. so that the full manifestation of the disease diabetes can be prevented under some circumstances.

This invention also includes a system to determine for a sample to which extent a sample belongs to a class in order to characterize a health condition. The system includes a memory unit for storing the signals of an electromagnetic spectrum generated by measuring an unknown sample and picked up by a detector. The system also includes an analyzer unit for generating a sample parameter via a multivariate analytical method based on the signals of the electromagnetic spectrum. By means of an analyzer unit, the sample parameter is allocated to a data record. This data record is obtained from the interpolation between at least one part of first data and at least one part of second data, each being allocated, respectively, to a first class and a second class. The first and second data, respectively, includes a first parameter and second parameter belonging to the first class and second class, respectively. These parameters have been generated by the multivariate analytical method on the basis of electromagnetic spectra of known samples belonging to the particular class, so that a reliable allocation of samples to the particular class is possible on the basis of the particular parameter. This data record is advantageously stored in a permanent memory of the memory unit. However it is also conceivable for the memory unit to contain a permanent memory in which only a first and second parameter, belonging to a first and a second class, respectively, are stored. The interpolated data record is calculated then as needed. The analyzer unit also determines a proportion value of the sample parameter in relation to at least a part of the data record. This proportion value indicates a proportion of the sample parameter in a class so that the extent to which the unknown sample belongs to that class is determined. An output unit shows the relation of a sample to a class. Data on more than two classes is advantageously stored in the system, so that a system is able to provide suggested diagnoses for a plurality of different diseases and disease courses. In a preferred embodiment, the system also includes a radiation source for directing electromagnetic radiation at a sample with electromagnetic radiation and a detector which detects the radiation interacting with the sample. If the radiation source emits electromagnetic radiation in the infrared range, for example, then the detector will advantageously detect signals in the range of 1 µm to 25 µm. Other advantageous embodiments of this system are also derived as described above.

BRIEF DESCRIPTION OF THE DRAWINGS

Exemplary embodiments of the invention are explained in greater detail below on the basis of figures without hereby resulting in any restrictive effect.

DETAILED DESCRIPTION

Figure 1:
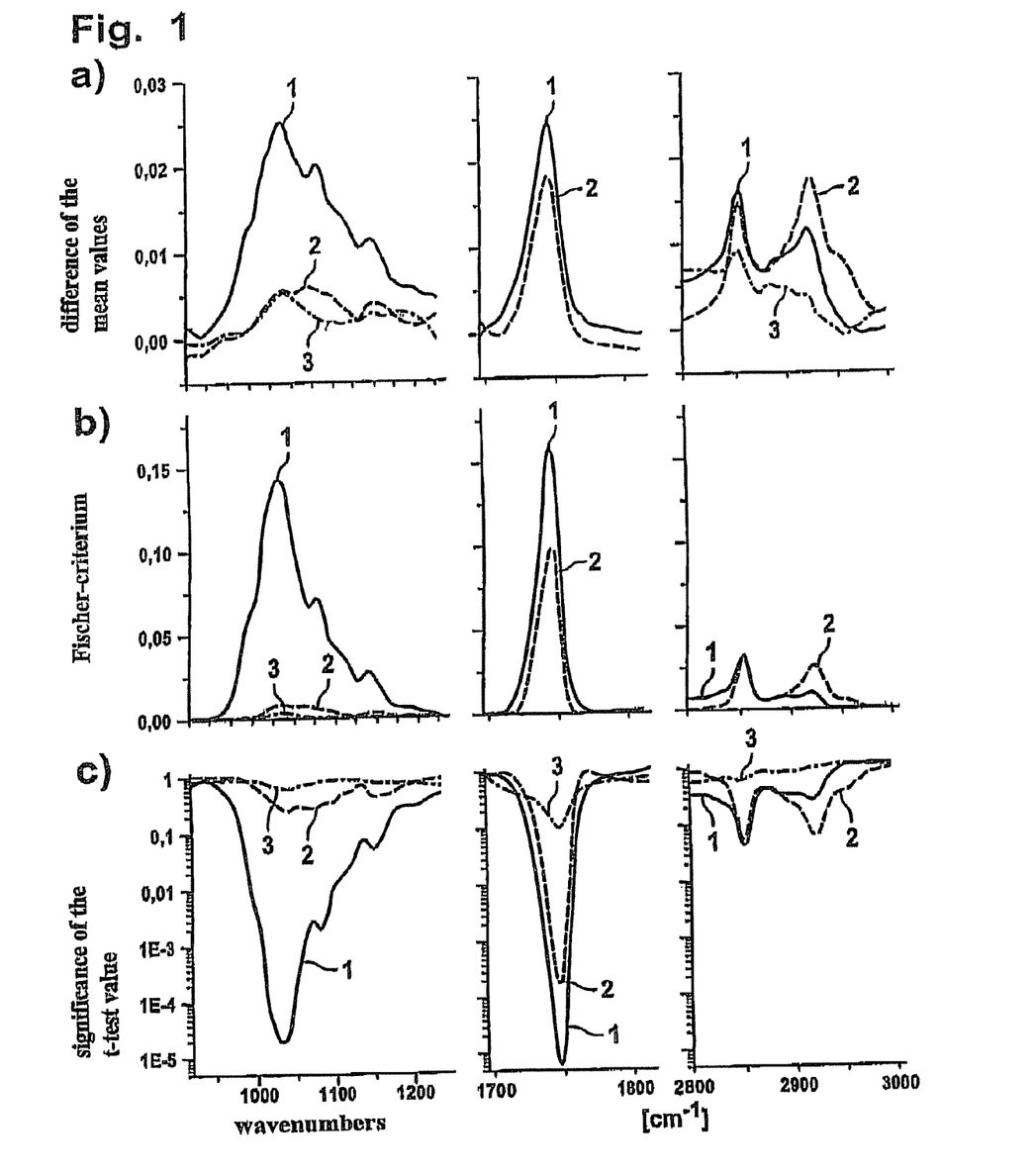
FIG. 1 shows spectral data on a sample of a healthy person in comparison with samples of a person with diabetes and a person with metabolic syndrome.

FIG. 1 shows various analyses of spectral data generated in performing measurements on samples of a healthy person, a patient with metabolic syndrome and a diabetic. The corresponding samples and the classes in this regard are referred to below for the sake of simplicity as healthy, metabolic syndrome and diabetes.

FIGS. 1a through 1c each show characteristic wavenumber ranges between 900 cm$^{-1}$ and 1,200, 1,700 to 1,800 cm$^{-1}$ and 2,800 to 3,000 cm$^{-1}$. Curve 1 in FIG. 1 shows the difference between the data from a healthy person and a diabetic, while curve 2 shows the difference between data from a healthy subject and a patient with metabolic syndrome. Curve 3 illustrates the differences in spectra that are obtained between the data from two healthy subjects generated by random differences.

FIG. 1a shows the particular curve in the aforementioned wavenumber ranges, each derived from the difference in the mean values of the data points. To be able to obtain a better differentiation between the different states, known statistical methods of analysis are used in the prior art. Among other things, the significance of differentiating criteria in the spectra is evaluated. For example, one conventional method is to compare the (squared) mean values with the (squared sum of) the standard deviations of the respective wavelength.

FIG. 1b shows how the so-called Fischer criterion is applied to the suitably selected wavenumber ranges. The Fischer criterion allows weighting of the resulting differences in the spectra. To do so, the deviation in two curves, each belonging to a different class, is represented in relationship to the particular standard deviation within the class. However, no statistical significance of the resulting differences is taken into account.

To calculate the significance of spectral differences, the analytical method conventionally known as a t-test in the prior art is used; this test includes the number of samples measured in the calculation. FIG. 1c shows a corresponding graph in which the t-test value is plotted as a function of the aforementioned wavenumber ranges. As shown by the shape of the curve in the wavenumber ranges shown here, a differentiation is possible with the help of statistical methods of analysis and thus it is possible to make clear-cut classification of samples into the classes of healthy, metabolic syndrome and diabetes.

Figure 2:
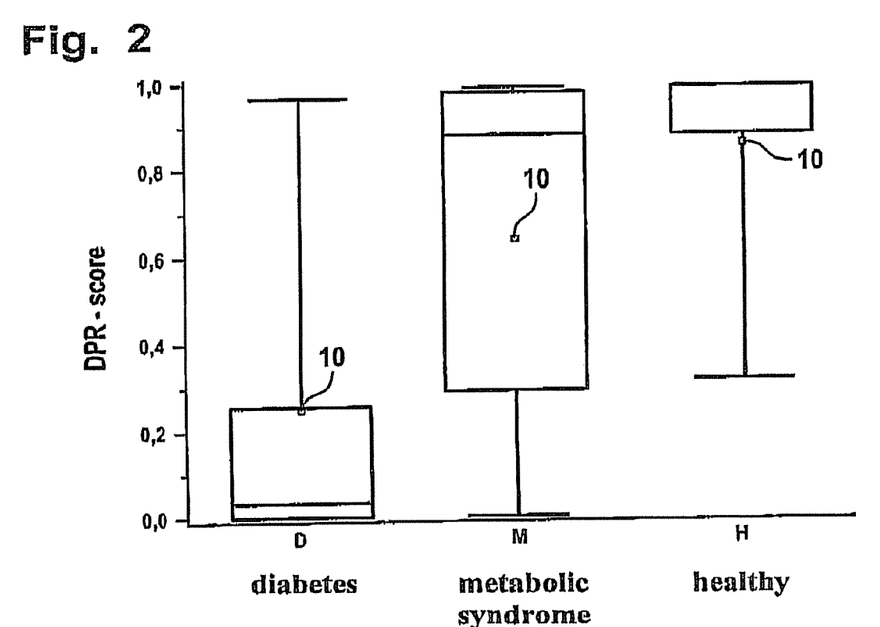
FIG. 2 shows a comparison of the DPR score obtained on the basis of samples of a healthy person, a person with metabolic syndrome and a person with diabetes.

FIG. 2 shows the various classes for the data corresponding to FIG. 1. For the classification, the data has been analyzed by means of a multivariate analytical method so that in each case one parameter was generated that can be allocated to the particular class. Within the scope of the present invention, the parameters thus calculated are referred to as the DPR score according to which a standardization of the parameters has been performed. The standardization of the DPR score is selected so that a DPR score of 0 gives a suggested diagnosis of diabetes and a DPR score of 1 was generated by a sample from a healthy patient. If there is a subdivision of the states diabetes, metabolic syndrome and healthy into three independent classes for each, the result for the diabetes class is an average (10) DPR score of 0.25, an average (10) of 0.65 for metabolic syndrome and an average (10) of 0.87 for the "healthy" class. In the box and whiskers plot shown here, the lower edge of the box denotes a DPR score below this value of 25% of the parameters. The middle line in the box is referred to as the median, where 50% of the parameters are below this value; 75% of the parameters can be allocated to a DPR score below the upper edge of the box. In addition, the respective error bars in the diagram indicate the range in which 90% of the parameters are located. As the data presented in this way indicate, approximately 75% of the parameters in the diabetes class are lower than 0.25, so a clear-cut allocation of these samples to this class is possible. Accordingly, 50% of the data from the metabolic syndrome class is below the DPR score of 0.87; 75% of the data belonging to the healthy class is above a DPR score of 0.87. As this diagram shows as an example, 50% of the data of the metabolic syndrome class is in the DPR score range >0.87, which also allows an allocation to the healthy class. These classes consequently have an intersection of data, whereby an allocation of a sample parameter to this intersection is impossible in the prior art.

According to this invention, however, an unknown sample is allocated to a data record calculated by interpolation between the data of the "healthy" class and the data of the "diabetes" class, for example. In the example shown here, the data is interpolated by performing an interpolation between the DPR scores of the particular classes. If there is an interpolation between the DPR scores of the healthy class and the diabetes class, the result is a curve which advantageously reflects the course of the disease diabetes. It is found here that the DPR score of the metabolic syndrome class can be allocated to the interpolated data record between the healthy class and the diabetes class. In this way, a correlation among the three different classes becomes clear, allowing conclusions regarding a medical correlation of the diseases. Consequently, the diagnosis of metabolic syndrome is to be classified in the course of the disease diabetes according to the analysis and thus can be regarded as a precursor of the disease diabetes.

Figure 3:
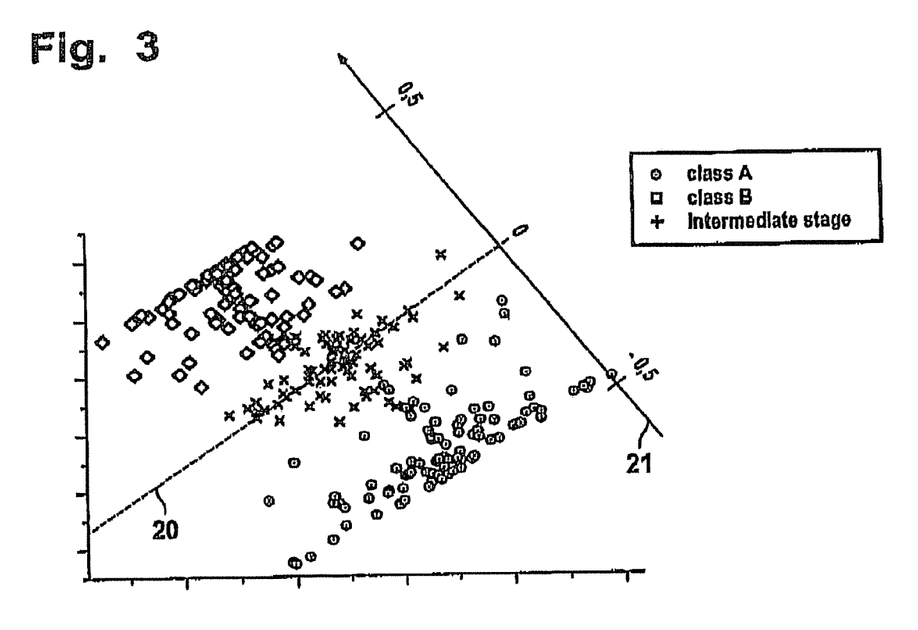
FIG. 3 shows parameter distribution of two classes.

FIG. 3 shows a plot of two main components of a multivariate analytical method generated in analysis of a sample. A plot of the main components of a multivariate analytical method, showing one as a function of the other, allows a characterization of ranges, each of which can be allocated to a class A or class B. The data points depicted as a rectangle are in the range of class B and the data points depicted as a circle show the range of class A. The discriminance function (20) delineates the ranges of the particular classes. In a range in the immediate vicinity of the discriminance function, an allocation to class A or B can no longer be made unambiguously. In this range, each data point is indicated with a cross. These data points form an intersection between classes A and B, which could not be allocated to a class by known methods in the prior art.

Figure 4:
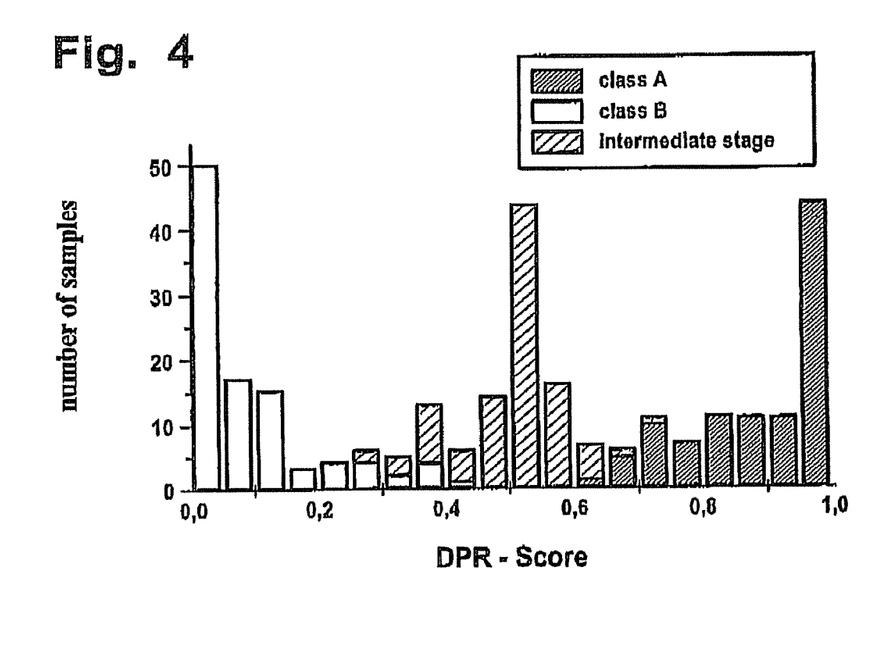
FIG. 4 shows a bar diagram illustrating the interpolation between the DPR scores.

FIG. 4 shows a quantification of the disease state derived from this, obtained from an interpolation between the DPR scores of class A and class B. The number of samples measured is plotted as a function of the calculated DPR score. It is found here that a considerable portion of samples is in the range of the intersection, so that in the prior art, it is impossible to make an allocation to one class. With the help of the inventive method, it is possible to allocate these samples to the disease course illustrated with no problem. A sample with a DPR score of 0.6 may thus give the diagnostic indication that a patient has a certain risk of developing a disease of class A. This risk may be expressed as a percentage, for example, so a DPR score of 0.6 indicates a 60% probability of developing a class A disease. In the example shown here, a DPR score of 0 is allocated to class B and a DPR score of 1 is allocated to class A. Alternatively, the distance of a data point from the discriminance function as illustrated in FIG. 3 may be used to determine the proportion value. The distance (21) here is calculated as a plumb line to the discriminance function according to the range from 1 to 0 between class A and class B spanned by the DPR score. Likewise, such relationships can be illustrated in a graph.

Figure 5:
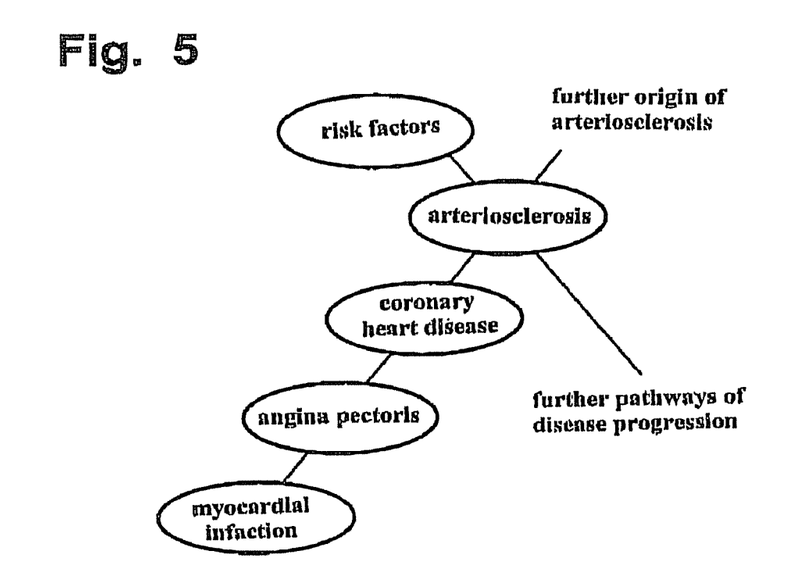
FIG. 5 shows Braunwald's cycle.
Figure 6:
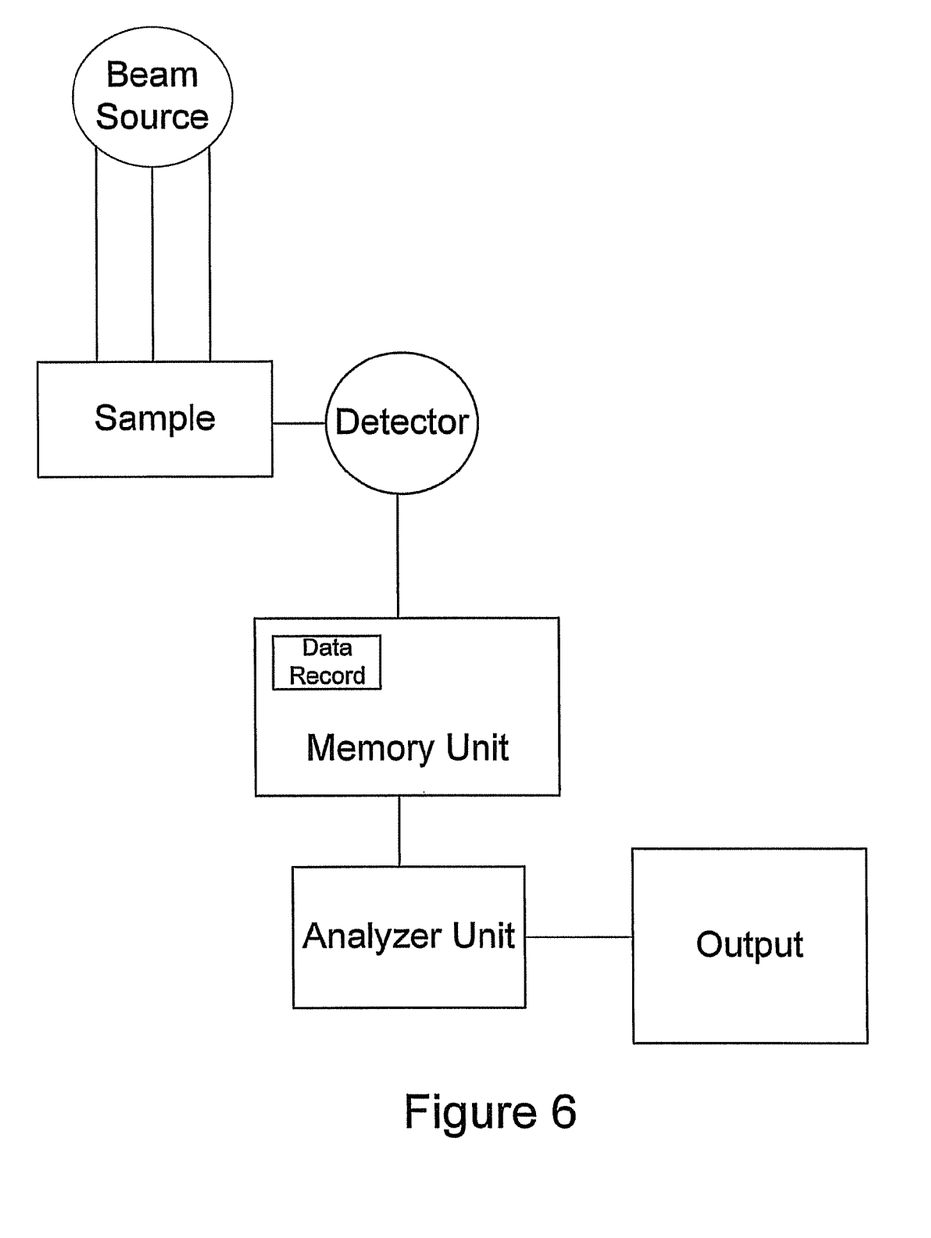
FIG. 6 shows a device for analying a sample.

FIG. 5 shows the plot of a disease course described as Braunwald cycle in the prior art (*Circulation*, 80 (1989) 410-414). Braunwald's cycle is a manifestation of a coronary heart disease and thus reflects correlations among different disease states. Starting from specific risk factors or other early stages of a disease, the disease course is manifested first with the symptoms of arteriosclerosis. If arteriosclerosis is diagnosed, this disease state may initially still have a nonspecific course. At this point in time there is still no definite correlation with a serious heart disease. However, if arteriosclerosis develops into coronary heart disease, angina pectoris may be induced by this condition. According to Braunwald's cycle, this disease state may then result in a myocardial infarction.

With the help of the inventive method, it is possible to determine directly the correlations between diseases such as those which can already be detected on the basis of clinical tests in Braunwald's cycle by interpolation between a healthy state and a diseased state. This makes it possible to obtain suggested diagnoses easily. In addition, correlations between different diseases can also be recognized according to a Braunwald cycle. For example, this makes it possible to diagnose diseases at an early stage of disease. Early detection of cancer-induced or TSE-induced pathological changes, such as BSE, are just a few examples which make the application of the inventive method appear to be especially advantageous.

The invention claimed is:

1. A system to determine for a sample the extent to which it belongs to a class so that a diagnostic indication of a health state can be given, comprising:
  a memory unit for storing the signals of an electromagnetic spectrum obtained by a detector, said signals being generated by measuring an unknown sample;
  an analyzer unit for
    (i) generating a sample parameter using a multivariate analytical method based on the signals of the electromagnetic spectrum and (ii) allocating the sample parameter to a data record calculated by interpolation between at least one part of a first data and at least one part of a second data, wherein
      the first and second data are allocated to a first and second class, respectively,
      the first data comprises a first parameter generated on the basis of electromagnetic spectra of known samples belonging to the first class using the multivariate analytical method so that a reliable allocation of samples to the first class on the basis of the first parameter is possible, and
      the second data comprises a second parameter generated on the basis of electromagnetic spectra of known samples belonging to the second class using the multivariate analytical method, so that a reliable allocation of samples to the second class is possible on the basis of the second parameter, and
    (iii) determining a proportion value for the sample parameter regarding at least a part of the data record, wherein the proportion value reflects a relation of the sample parameter to a class in such a way that it can be determined to what extent the unknown sample belongs to a class; and
  an output unit for display of the relation of a sample to a class.

2. The system according to claim 1, wherein the first and second parameters are stored in a permanent memory of the memory unit.

3. The system according to claim 1, wherein the data record is stored in a permanent memory of the memory unit.

4. The system according to claim 1, wherein data for more than two classes is stored.

5. An analysis system comprising a system according to claim 1, further comprising a beam source for irradiating a sample with electromagnetic radiation.

6. The analysis system according to claim 5, wherein the radiation source emits electromagnetic radiation in the IR range.

7. The system according to claim 1, farther comprising a detector for detecting radiation interacting with the sample.

8. The analysis system according to claim 7, wherein the detector detects signals in the range of 1 µm to 25 µm.

9. A method of analyzing an electromagnetic spectrum, wherein a proportionate relation of the electro-magnetic spectrum to a class is determined to provide a diagnostic indication for a health status, comprising:
  determining a sample parameter using a multivariate analytical method based on an electromagnetic spectrum generated by measurement of an unknown sample;
  allocating the sample parameter to a data record calculated by interpolation between at least one part of first data and at least one part of second data, wherein
    the first and second data are allocated to a first and second class, respectively,
    the first data comprises a first parameter which has been generated on the basis of electromagnetic spectra of known samples belonging to a first class using the multivariate analytical method so that a reliable allocation of samples to the first class is possible on the basis of the first parameter, and
    the second data comprises a second parameter generated on the basis of electromagnetic spectra of known samples belonging to the second class using the multivariate analytical method so that a reliable allocation of samples to the second class is possible on the basis of the second parameter; and
  determining a proportion value for the sample parameter regarding at least a part of the data record, the proportion value reflecting a relation of the sample parameter to a class in such a way that it can be determined to what extent the unknown sample belongs to a class.

10. The method according to claim 9, wherein the first class characterizes a health status of a patient having diabetes and the second class characterizes a health status of a patient not having diabetes, and the data record includes a sample parameter generated by a sample of a patient having metabolic syndrome.

11. The method according to claim 9, wherein the interpolation is performed between the first parameter and the second parameter.

12. The method according to claim 9, wherein the relation of a sample parameter of a class is calculated as a percentage proportion.

13. The method according to claim 9, wherein a correlation is formulated between the data record and the progression of a disease.

14. The method according to claim 9, wherein a linear discriminant analysis is performed as part of the multivariate analytical method.

15. The method according to claim 9, wherein neural networks are used as part of the multivariate analytical method.

16. The method according to claim 9, wherein the diagnostic indication contributes toward early detection of cancer-induced and TSE-induced pathological anomalies.

17. The system according to claim 1 configured to employ a method of analyzing an electromagnetic spectrum, wherein a proportionate relation of the electromagnetic spectrum to a class is determined to provide a diagnostic indication for a health status, the method comprising:
  determining the sample parameter using the multivariate analytical method based on an electromagnetic spectrum generated by measurement of an unknown sample;
  allocating the sample parameter to the data record calculated by interpolation between at least one part of first data and at least one part of second data; and
  determining the proportion value for the sample.

18. The method according to claim 9, being executed on a system comprising:
  a memory unit for storing signals of the electromagnetic spectrum obtained by a detector, said signals being generated by measuring the unknown sample;
  an analyzer unit; and
  an output unit for display of the relation of a sample to a class.

19. A computer-readable medium having stored thereon instructions executable by a processor to perform functions to diagnose individual stages of a progression of a disease, the functions including:

creating a data record which is calculated by interpolation between at least one part of first data and at least one part of second data, wherein
   the first data and the second data are allocated to a first class and a second class, respectively,
   the first data comprises a first parameter which has been generated on the basis of electromagnetic spectra of known samples belonging to the first class of using a multivariate analytical method so that a reliable allocation of samples to the first class is possible on the basis of the first parameter, and
   the second data includes a second parameter generated on the basis of electromagnetic spectra of known samples belonging to the second class using the multivariate analytical method so that a reliable allocation of samples to the second class is possible on the basis of the second parameter, generating a sample parameter of an unknown sample using a multivariate analytical method based on an electromagnetic spectrum;

determining a proportion value for the sample parameter regarding at least a part of the data record, wherein the proportion value reflects a relation of the sample parameter to a class in such a way that it can be determined to what extent the unknown sample belongs to a class; and allocating the sample parameter to the data record.

\* \* \* \* \*